(12) United States Patent
McDonald (10) Patent No.: US 10,864,009 B2
(45) Date of Patent: Dec. 15, 2020

(54) VALVE CUTTER

(71) Applicant: Michael B. McDonald, Cordova, TN (US)

(72) Inventor: Michael B. McDonald, Cordova, TN (US)

( * ) Notice: Subject to any disclaimer, the term of this patent is extended or adjusted under 35 U.S.C. 154(b) by 476 days.

(21) Appl. No.: 15/295,615

(22) Filed: Oct. 17, 2016

(65) Prior Publication Data

US 2017/0027600 A1     Feb. 2, 2017

Related U.S. Application Data

(63) Continuation-in-part of application No. 14/097,874, filed on Dec. 5, 2013, now Pat. No. 9,468,458.

(60) Provisional application No. 61/733,803, filed on Dec. 5, 2012.

(51) Int. Cl.

| | |
|---|---|
| *A61B 17/32* | (2006.01) |
| *A61M 29/00* | (2006.01) |
| *A61B 17/3207* | (2006.01) |
| *A61B 90/00* | (2016.01) |
| *A61B 17/22* | (2006.01) |

(52) U.S. Cl.
CPC ............... *A61B 17/32002* (2013.01); *A61B 17/320758* (2013.01); *A61B 17/320783* (2013.01); *A61M 29/00* (2013.01); *A61B 2017/22071* (2013.01); *A61B 2017/22097* (2013.01); *A61B 2017/320004* (2013.01); *A61B 2017/320028* (2013.01); *A61B 2090/064* (2016.02)

(58) Field of Classification Search
CPC . A61B 17/22; A61B 17/3205; A61B 17/3207; A61B 17/320016; A61B 17/32002; A61B 17/320758; A61B 17/320783; A61B 2017/22052; A61B 2017/320791
USPC ......................................................... 606/167
See application file for complete search history.

(56) References Cited

U.S. PATENT DOCUMENTS

| | | | | |
|---|---|---|---|---|
| 4,994,067 A | * | 2/1991 | Summers ....... | A61B 17/320758 604/22 |
| 5,188,635 A | * | 2/1993 | Radtke .................. | A61B 17/22 606/14 |
| 5,431,673 A | * | 7/1995 | Summers ....... | A61B 17/320758 606/167 |

(Continued)

FOREIGN PATENT DOCUMENTS

WO          WO 8906935         *    8/1989

*Primary Examiner* — Wade Miles
*Assistant Examiner* — Kankindi Rwego
(74) *Attorney, Agent, or Firm* — Angela Holt; Bradley Arant Boult Cummings LLP (57) ABSTRACT

A cardiac valve cutter of the present disclosure has a flexible housing with a central lumen for receiving a guide wire. A high-speed cutting blade is disposed within the housing near an edge of the housing. A trough cut into a side of the housing exposes a portion of the cutting blade so that the cutting blade can cut valve tissue. Two pusher wires are disposed on an opposite side of the housing from the cutting blade. Troughs cut into the side of the housing form openings from which the pusher wires can extend. The pusher wires are staggered with respect to one another in the longitudinal direction. When the pusher wires are advanced, they extend outwardly from the troughs and can be used to stabilize the cutter at the cardiac valve and push the cutting blade against the valve on the opposite side.

10 Claims, 5 Drawing Sheets

(56) References Cited

U.S. PATENT DOCUMENTS 5,584,842 A * 12/1996 Fogarty .......... A61B 17/320725
606/159
6,936,024 B1 * 8/2005 Houser .............. A61B 18/1492
604/22

* cited by examiner

Fig. 1

Fig. 2
(Sec. A-A)

Fig. 3
(Sec. B-B)

Fig. 4
(Sec. C-C)

Fig. 8
(Sec. D-D)

Fig. 10
(Sec. E-E)

Fig. 11
(Sec. F-F)

Fig. 12
(Sec. G-G)

VALVE CUTTER

CROSS REFERENCE TO RELATED APPLICATIONS

This application is a continuation-in-part of U.S. Non-provisional Application Ser. No. 14/097,874 titled "Aortic Valve Cutter, filed on Dec. 5, 2013, which application claims priority to U.S. Provisional Application Ser. No. 61/733,803, titled "Aortic Valve Cutter," filed on Dec. 5, 2012. The entire contents of U.S. Non-provisional Application Ser. No. 14/097,874 and U.S. Provisional Application Ser. No. 61/733,803 are herein incorporated by reference.

BACKGROUND AND SUMMARY OF THE INVENTION

Aortic stenosis, an abnormal narrowing of the aortic valve, is the most common valve disease in the world. Patients with aortic stenosis experience restricted blood flow from the heart and suffer increased risk of heart failure. Currently available treatments for aortic stenosis include surgical valve replacement, transcatheter valve replacement, and balloon aortic valvuloplasty. In surgical valve replacement, the patient undergoes open heart surgery to replace the stenotic valve. A transcatheter valve replacement (TAVR), in which the valve is replaced in transcatheter procedure, is a less invasive approach to replacing the stenotic valve. Balloon aortic valvuloplasty does not replace the valve, but rather a balloon catheter is inflated within the aortic valve to increase the size of the opening.

Each of these existing treatments has advantages and drawbacks. The drawbacks of the surgical approach include the obvious risks of such major surgery. Drawbacks of the TAVR and balloon aortic valvuloplasty include having the heart undergo short and rapid ventricular pacing during portions of the procedure and risks inherent in implementation of a foreign device into the heart. Further, the costs of the surgical valve replacement and TAVR are quite high. The balloon aortic valvuloplasty produces improvements in the aortic stenosis, but the improvements typically last only a few months. What is desired is a lower cost, safer minimally-invasive procedure to increase the opening of a stenotic valve.

A cardiac valve cutter of the present disclosure comprises a flexible housing with a central lumen for receiving a guide wire. A high-speed rotating wire is disposed within the housing near an edge of the housing. A trough cut into a side of the housing exposes a portion of the rotating wire such that the rotating wire can be used as a cutter. Two pusher wires are disposed on an opposite side of the housing from the rotating wire, also housed within the housing. Troughs cut into the side of the housing form openings from Which the pusher wires can extend if they are advanced. The pusher re staggered with respect to one another in the longitudinal direction. When the pusher wires are advanced, they extend outwardly from the troughs and can be used to stabilize the cutter at the aortic valve and push the cutting wire against the valve on the opposite side.

Two wire pressure transducers are disposed on the housing, one above the rotating wire and another below the rotating wire. These transducers allow for monitoring of the pressure gradient across the valve as the cutting proceeds. By monitoring the transvalve gradient while the cuts are made to the aortic valve, the aortic valve area can be estimated during the procedure.

In another embodiment, instead of a rotating wire, the device uses a cutting blade, e.g., a reciprocating saw blade. The device can be used for aortic valve, mitral valve, and tricuspid valve procedures.

For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

The disclosure can be better understood with reference to the following drawings. The elements of the drawings are not necessarily to scale, emphasis instead being placed upon clearly illustrating the principles of the disclosure. Furthermore, like reference numerals designate corresponding parts throughout the several views.

DETAILED DESCRIPTION

Figure 1:
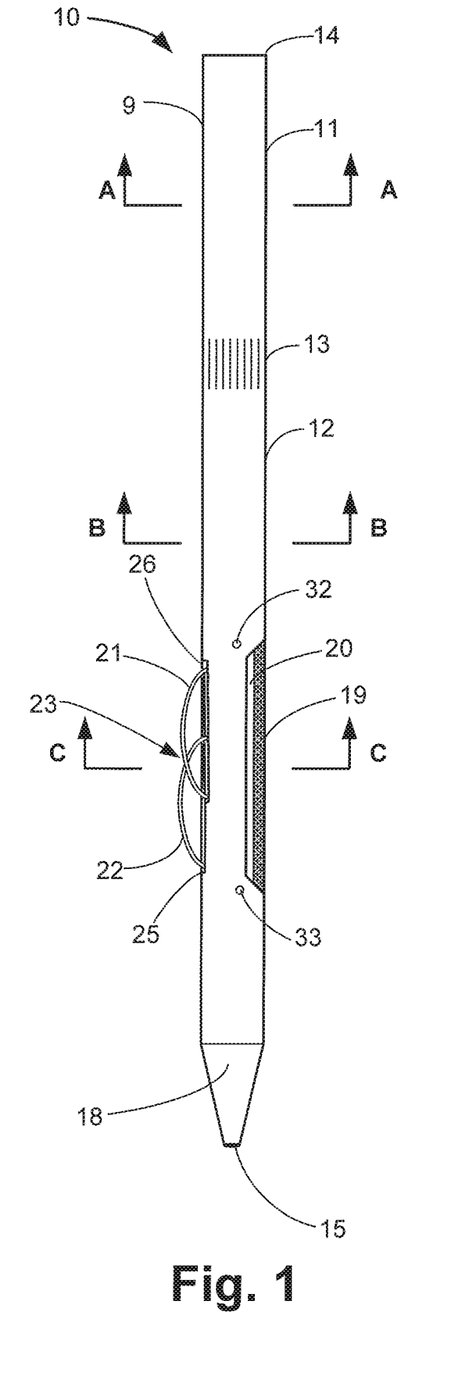
FIG. 1 is a front plan view of an embodiment of an aortic valve cutter in accordance with the present disclosure.

FIG. 1 is a front perspective view of an aortic valve cutter 10 according to an exemplary embodiment of the present disclosure. In this embodiment, the valve cutter 10 comprises an elongated housing 9 with a central lumen 17 (FIG. 2) extending through the housing 9 for receiving a guide wire (not shown). An upper opening (not shown) is disposed in an upper end 14 of the housing 9 and a lower opening (not shown) is disposed in a distal end 15 of the housing 9. The guide wire passes through the upper opening, the lumen, and the lower opening. The lumen 17 and openings allow the cutter 10 to be advanced through an artery and across the aortic valve in an over-the-wire fashion.

In the illustrated embodiment, the housing 9 is formed in one piece from flexible material such as the tubing currently used to form cardiac catheters. The housing 9 comprises a generally cylindrical upper portion 11 and a generally elliptical lower portion 12. A transition portion 13 transitions the housing 9 from the generally cylindrical (round) shape of the upper portion 11 to a generally elliptical shape of the lower portion 12. A narrowed tip 18 is disposed at the distal end 15 of the housing 9. The tip 18 is tapered for ease in passing the cutter 10 through the aortic valve.

The cutter 10 further comprises a cutting wire 19. The cutting wire 19 extends longitudinally down the housing 9 and is substantially parallel with a longitudinal axis of the housing 9. The cutting wire is accessible via a cutting trough 20. In this regard, the cutting trough 20 comprises an elongated opening in an outer wall of the housing 9 in the elliptical lower portion 12 of the housing 9. The cutting wire 19 is disposed near an outer edge (not shown) of the housing 9 such that the cutting wire 19 is exposed for the length of the cutting trough 20.

The cutting wire 19 is a diamond-coated wire in one embodiment, and rotates at a high speed when the cutter 10 is in operation. The rotation of the cutting wire 19 is effectuated by a motor (not shown) that turns a rotating wire (not shown) that extends through the upper end 14 of the cutter 10 into the housing 9 and rotates the cutting wire 19. The motor may be any of a number of pneumatic or electrical motors known in the art.

An upper pusher wire 21 and a lower pusher wire 22 are disposed on an opposite side of the housing 9 from the cutting wire 19. The upper pusher wire 21 and the lower pusher wire 22 each comprise wires that extend longitudinally through the upper end 14 of the cutter 10 and into the housing 9. The upper pusher wire 21 and the lower pusher wire 22 are each substantially parallel with a longitudinal axis of the housing 9. The upper pusher wire 21 is disposed within an upper trough 26 and the lower pusher wire 22 is disposed within a lower trough 25. The upper trough 26 and the lower trough 25 each comprise elongated openings in the housing 9 through which the pusher wires 21 and 22 are extendible. In this regard, the pusher wires 21 and 22 are in a retracted orientation (i.e., not extended) during insertion of the cutter 10 within the patient's aortic valve. When the pusher wires 21 and 22 are in the retracted orientation, the pusher wires 21 and 22 are substantially parallel to the cutting wire 19.

Advancing the pusher wires 21 and 22 causes them to extend from the troughs 26 and 25 as shown in FIG. 1. The pusher wires 21 and 22 are thus extendable and retractable in the direction shown by directional arrows 30 and 31. The advancing mechanism (not shown) for the pusher wires is of a type known in the art, such as a track bar with a thumb driven slide or a small rotating wheel.

The upper trough 26 is located upwardly from the lower trough 25 such that the pusher wires 21 and 22 are staggered as shown The upper trough 26 is disposed closely beside the lower trough 25 such that the wires 21 and 22 are spaced closely together. When the pusher wires 21 and 22 are extended as shown in FIG. 1, a valley 23 is formed bet the outermost points of the pusher wires 21 and 22. This valley 23 can be used to help position the valve cutter 10 when it is in use, as further discussed herein with respect to FIG. 7. Note that the valley 23 is generally aligned with the longitudinal center of the cutting wire 19. This means that when the valley 23 is contacting a portion of the aortic valve, the center of the cutting wire 19 should be aligned with an opposite portion of the aortic valve.

The illustrated embodiment comprises two pusher wires, i.e., the upper pusher wire 21 and the lower pusher wire 22. Other embodiments may comprise more or fewer pusher wires.

The cutter 10 further comprises an upper transducer 32 and a lower transducer 33. The upper transducer 32 is located above the cutting wire 19 and the lower transducer 33 is located below the cutting wire 19. The upper and lower transducers 32 and 33 are of a type known in the art for measuring the pressure inside a patient's heart. In use of the cutter 10, the upper transducer 32 is typically used to measure the aortic pressure and the lower transducer 33 is used to measure the pressure in the left ventricle, as is discussed further herein.

Figure 2:
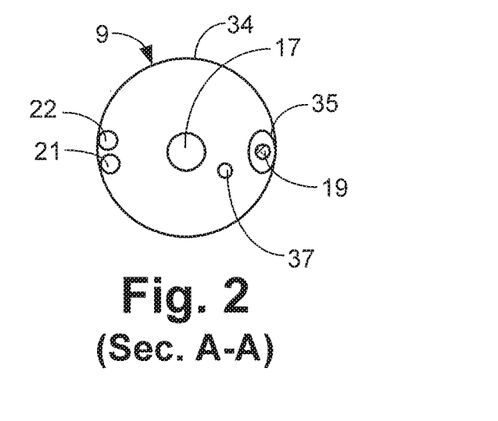
FIG. 2 is a cross sectional view of the aortic valve cutter of FIG. 1, taken along section lines A-A.

FIG. 2 is a cross-sectional representation of the upper portion 11 of the cutter 10 of FIG. 1, taken along section lines A-A. An outer wall 34 extends generally circularly around the perimeter of the housing 9. The upper portion has a diameter of 14 French in one embodiment, though other sizes may be used. The lumen 17 is centrally disposed within the housing 9. The cutting wire 19 is disposed near the outer wall 34, within a sheath 35. The sheath 35 is generally oval or cylindrical in shape and extends down through the housing 9. In the illustrated embodiment, the sheath 35 surrounds the cutting wire 19 down the length of the housing 9, except where the cutting trough 20 (FIG. 1) is located.

The pusher wires 21 and 22 are located on an opposite side from (i.e., generally 180 degrees apart from) the cutting wire 19 in the illustrated embodiment. The pusher wires 21 and 22 are located close together and very close to the edge of the external wall 36 as shown. This arrangement enables the pusher wires 21 and 22, where they extend from the troughs 26 and 25 (FIG. 1), to push against the aortic valve leaflets (not shown) to assist in stabilizing the cutter 10 and advancing the cutting wire 19 toward the tissue being cut, as further discussed herein.

A transducer wire 37 extends through the housing 9 to the upper and lower transducers 32 and 33.

Figure 3:
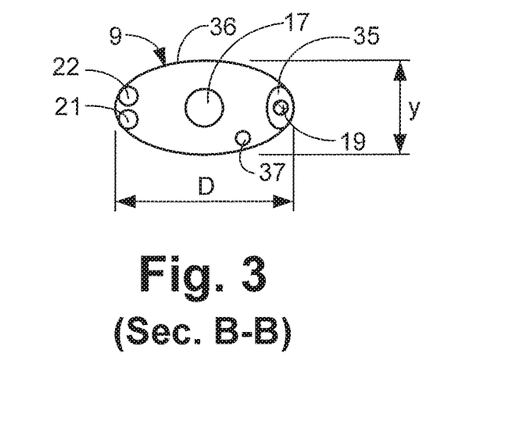
FIG. 3 is a cross sectional view of the aortic valve cutter of FIG. 1, taken along section lines B-B.

FIG. 3 is a cross-sectional view of the elliptical portion 12 of the cutter 10 of FIG. 1, taken along section lines B-B. In the elliptical portion 12, an outer wall 36 is ovally shaped, with the cutting wire 19 and the pusher wires 21 and 22 disposed on opposite outermost sides of the oval as shown. The width "D" of the elliptical portion 12 of the cutter 10 is the same as the diameter of the upper portion 11 in the illustrated embodiment. The short side "y" of the elliptical portion 12 of the cutter 10 is substantially less than the width "D."

Figure 4:
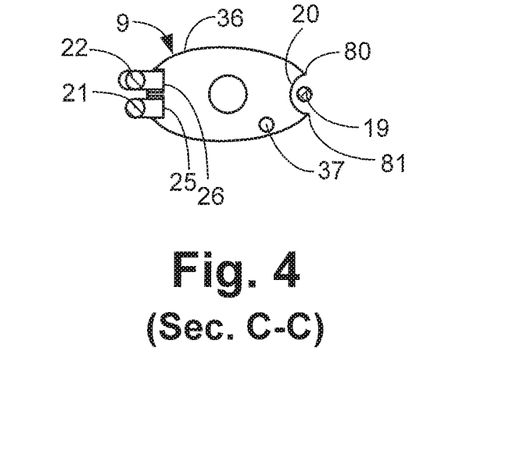
FIG. 4 a cross sectional view of the aortic valve cutter of FIG. 1, taken along section C-C.

FIG. 4 is a partial cross-sectional representation of the elliptical portion 12 of the cutter 10 of FIG. 1, taken along sections lines C-C. This figure shows the pusher wires 21 and 22 extended from the housing 9. In this extended position, the pusher wires 21 and 22 extend beyond the outer wall 36 as shown.

In this cross-sectional view, the cutting wire 19 appears as if it is extended from the cutting trough 20. However, the cutting wire 19 is generally vertically disposed within the housing 9. The cutting wire 19 rotates, but it does not typically bend. Because the outer wall 36 is cut away at the location of the cutting trough 20, the cutting wire 19 becomes the outermost surface at the location of the cutting trough 20, such that the cutting wire 19 may cut any tissue it contacts if the cutting wire 19 is rotating. In other words, the cutting wire extends further outwardly than opposed longitudinal edges 80 and 81 of the cutting trough 20.

Figure 5:
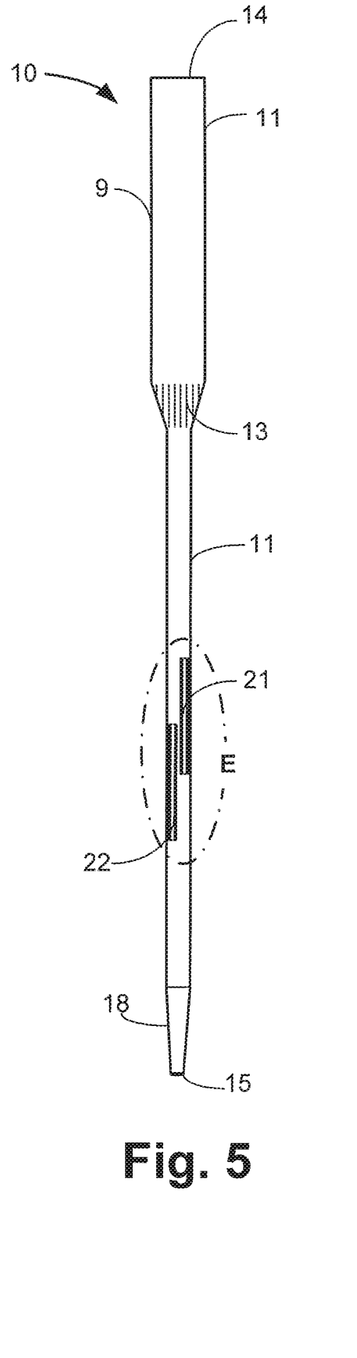
FIG. 5 is a right side plan view of the aortic valve cutter of FIG. 1.

FIG. 5 is a right side plan view of the cutter 10 of FIG. 1. Note that because the elliptical lower portion 12 of the housing 9 is elliptically shaped, the lower portion 12 is narrower than the upper portion 11 in this view.

Figures 5A, 6:
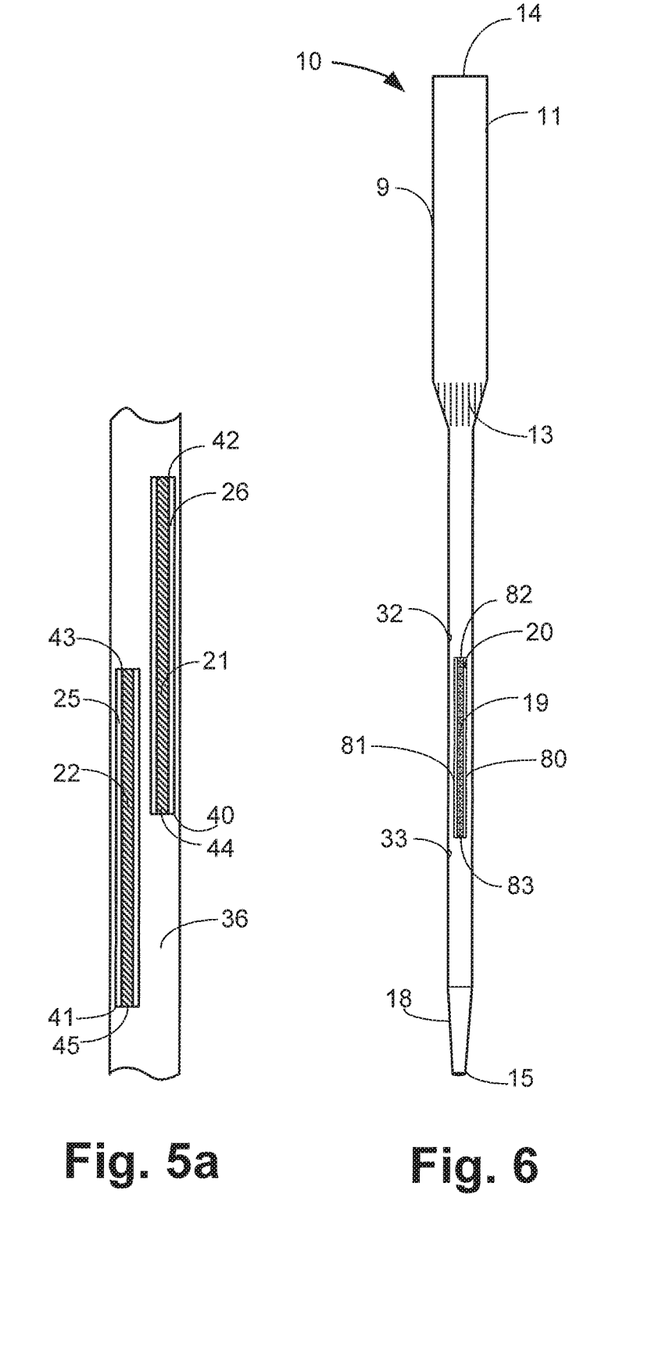
FIG. 5a is an enlarged view of the aortic valve cutter of FIG. 5, taken along line E of FIG. 5.
FIG. 6 is a left side plan view of the aortic valve cutter of FIG. 1.

FIG. 5a is an enlarged partial view of the cutter 10 of FIG. 5, taken along line "E" of FIG. 5. The upper trough 26 is disposed closely beside the lower trough 25, but is spaced above the lower trough 25 as shown; i.e., the troughs 26 and 25 are staggered in the longitudinal direction. The upper trough 26 is a generally rectangular cutout in the outer wall 36 and has an upper end 42 and a lower end 40. A lower end 44 of the pusher wire 21 is fixed at or near the lower end 40 of the upper trough 26. The lower end 44 of the pusher wire 21 being fixed enables the pusher wire 21 to extend from the trough 26 when the pusher wire 21 is advanced, and to retract from the trough 26 when the pusher wire 21 is retracted.

Similarly, the lower trough 25 is a generally rectangular cutout in the outer wall 36 and has an upper end 43 and a lower end 41. A lower end 45 of the pusher wire 22 is fixed at or near the lower end 41 of the lower trough 25. The lower end 45 of the pusher wire 22 being fixed enables the pusher wire 22 to extend from the trough 25 when the pusher wire 22 is advanced, and to retract from the trough 25 when the pusher wire 22 is retracted.

FIG. 6 is a left side plan view of the cutter 10 of FIG. 1. In this embodiment, the cutting trough 20 is a generally rectangularly shaped cutout in the outer wall 36. The cutting trough has a short top edge 82, a short bottom edge 83, and opposed longitudinal edges 80 and 01. In one embodiment, the cutting trough 20 is generally 2 centimeters in longitudinal length. The upper pressure transducer 32 is disposed above the cutting wire 20 and the lower pressure transducer 33 is disposed below the cutting trough 20.

Figure 7:
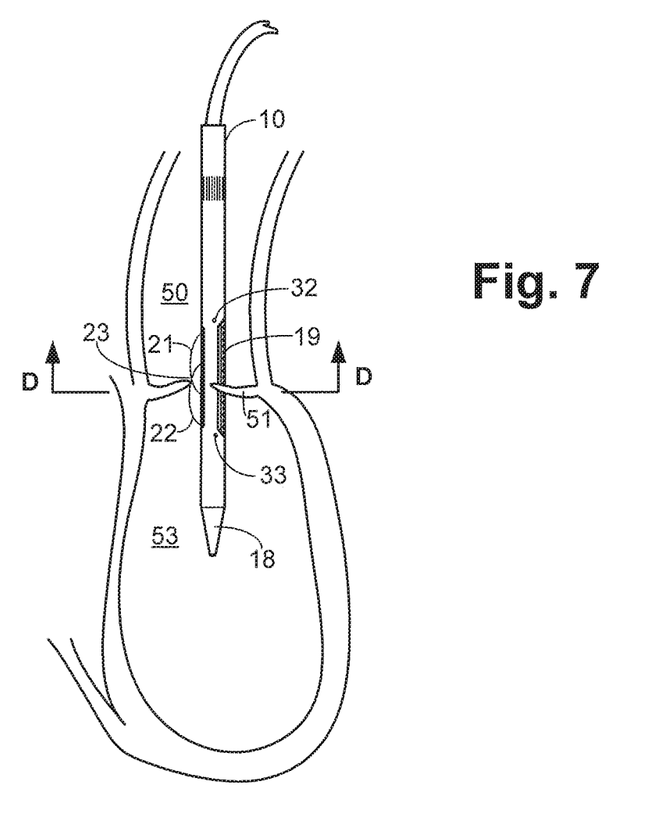
FIG. 7 depicts the aortic valve cutter of FIG. 1 being used to cut a stenosed aortic valve.

FIG. 7 depicts the aortic valve cutter of FIG. 1 being used to cut a stenosed aortic valve. To use the cutter 10, the cutter 10 is advanced transfemorally through the patient's aorta 50 and across the aortic valve 51, such that the tip 18 has entered the left ventricle cavity 53, Pressure measurements from the upper and lower transducers 32 and 33 can be used to position the cutter 10 across the aortic valve 51. In this regard, a normal pressure in the aorta (not shown) is around 120, and a normal pressure in the left ventricle cavity is around 50. When the upper transducer 32 measures a pressure known to be the aortic pressure and the lower transducer 33 measures a pressure known to be the left ventricular pressure, the cutter 10 will be known to be in position where the cutting wire 19 is in general alignment with the aortic valve annulus 51.

The cardiologist may then advance the pusher wires 21 and 22 to extend them from the cutter 10. To further align the cutter 10, the valley 23 between the upper pusher wire 21 and the lower pusher wire 22 may be aligned with the aortic annulus. In this regard, the cardiologist should be able to discern when an aortic leaflet 70a (FIG. 8) contacts the valley 23. Because the valley 23 is aligned with a central portion of the cutting wire 9, when the valley 23 is contacting a portion of the aortic valve 51, the center of the cutting wire 19 should be aligned. with an "opposite portion" of the aortic valve.

Figure 8:
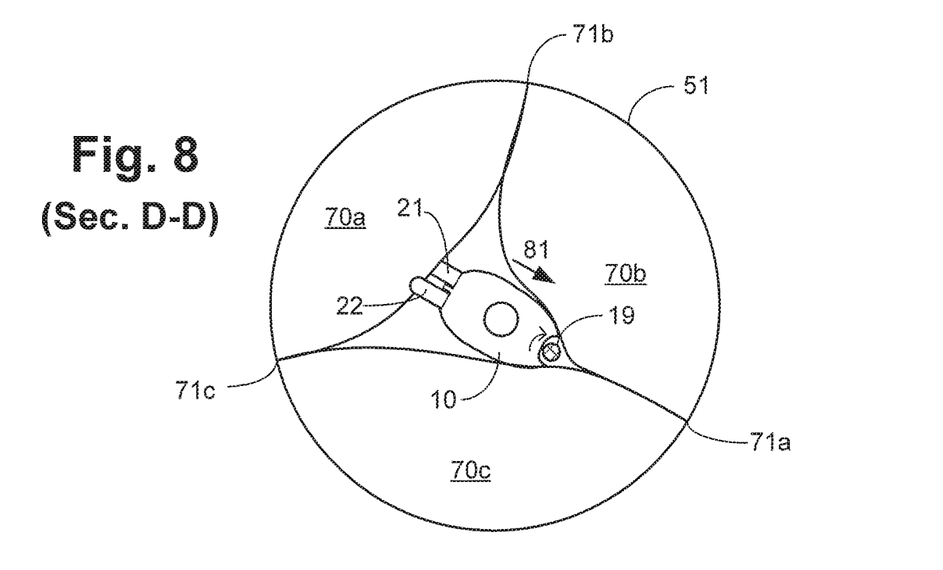
FIG. 8 is a cross sectional view of the aortic valve cutter of FIG. 7, taken along section lines D-D.

FIG. 8 is a cross sectional view of the cutter 10 of FIG. 7, with the cutter 10 in a patient's aortic valve, taken along section lines D-D. In this view the cutter pusher wires 21 and 22 are pressing against a leaflet 70a of the aortic valve 51. The pressing of the pusher wires 21 and 22 stabilizes the cutter within the aortic valve and also causes the cutter 10 to move in the direction indicated by directional arrow 81, such that the cutting wire 19 advances to cut along a commissure 71a between the leaflets 70b and 70c of the aortic valve 51.

The pressure readings from the upper and lower transducers 32 and 33 can be monitored during the cutting procedure. As the cuts are made to reduce the aortic stenosis, the systolic pressure reading from the lower transducer should begin to equalize with the reading from the upper transducer.

Figure 9:
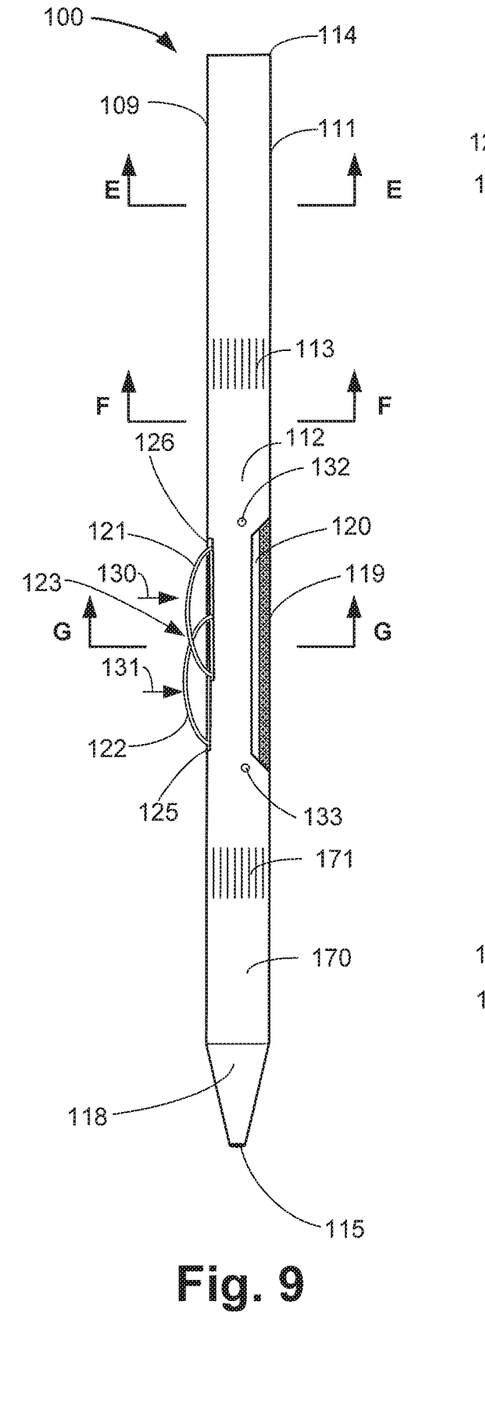
FIG. 9 is a front plan view of another embodiment of a cardiac valve cutter in accordance with the present disclosure.

FIG. 9 is a front perspective view of a cardiac valve cutter 100 according to another exemplary embodiment of the present disclosure. In this embodiment, the valve cutter 100 comprises an elongated housing 109 with a central lumen 117 (FIG. 10) extending through the housing 109 for receiving a guide wire (not shown). An upper opening (not shown) is disposed in an upper end 114 of the housing 109 and a lower opening (not shown) is disposed in a distal end 115 of the housing 109. The guide wire passes through the upper opening, the lumen, and the lower opening. The lumen 117 and openings allow the cutter 100 to be advanced through an artery and across the valve in an over-the-wire fashion.

In the illustrated embodiment, the housing 109 is formed in one piece from flexible material such as the tubing currently used to form cardiac catheters. The housing 109 comprises a generally cylindrical upper portion 111, a generally elliptical middle portion 112, and a generally cylindrical lower portion 170. A proximal transition portion 113 transitions the housing 109 from the generally cylindrical (round) shape of the upper portion 111 to a generally elliptical shape of the middle portion 112.

The upper portion 111 of the cutter 100 connects to flexible catheter tubing (not shown) that is known in the art. In one embodiment, the angle of flexing of the flexible catheter tubing can be controlled by a user using flex controls (not shown) that are known in the art. The flexing can produce a J-shaped distal configuration of the cutter 100 in use, which can be useful in making cuts in mitral valves or tricuspid valves by percutaneous access.

A distal transition portion 171 transitions the housing 109 from the generally elliptical shape of the middle portion 112 to the generally cylindrical shape of the lower portion 170. A narrowed tip 118 is disposed at the distal end 115 of the housing 109. The tip 118 is tapered fir ease in passing the cutter 100 through the cardiac valve.

The cutter 100 further comprises a cutting blade 119. The cutting blade 119 extends longitudinally down the housing 109 and is substantially parallel with a longitudinal axis of the housing 109. The cutting blade is accessible via a cutting trough 120. In this regard, the cutting trough 120 comprises an elongated opening in an outer wall of the housing 109 in the elliptical middle portion 112 of the housing 109. The cutting blade 119 is disposed near an outer edge (not shown) of the housing 109 such that the cutting blade 119 is exposed for the length of the cutting trough 120.

The cutting blade 119 is a reciprocating saw blade in this embodiment, and moves at high speed when the cutter 100 is in operation. The movement of the cutting blade 119 is effectuated by a motor (not shown). The motor may be any of a number of pneumatic or electrical motors known in the art.

An upper pusher wire 121 and a lower pusher wire 122 are disposed on an opposite side of the housing 109 from the cutting blade 119. The upper pusher wire 121 and the lower pusher wire 122 each comprise wires that extern longitudinally through the upper end 114 of the cutter 100 and into the housing 109. The upper pusher wire 121 and the lower pusher wire 122 are each substantially parallel with a longitudinal axis of the housing 109. The upper pusher wire 121 is disposed within an upper trough 126 and the lower pusher wire 122 is disposed within a lower trough 125. The upper trough 126 and the lower trough 125 each comprise elongated openings in the housing 109 through which the pusher wires 121 and 122 are extendible. In this regard, the pusher wires 121 and 122 are in a retracted orientation (i.e., not extended) during insertion of the cutter 100 within the patient's cardiac valve. When the pusher wires 121 and 122 are in the retracted orientation, the pusher wires 121 and 122 are substantially parallel to the cutting wire 109.

Advancing the pusher wires 121 and 122 causes them to extend from the troughs 126 and 125 as shown in FIG. 9. The pusher wires 121 and 122 are thus retractable in the direction shown by directional arrows 130 and 131. The advancing mechanism (not shown) for the pusher wires is of a type known in the art, such as a track bar with a thumb driven slide or a small rotating wheel.

The upper trough 126 is located upwardly from the lower trough 125 such that the pusher wires 121 and 122 are staggered as shown. The upper trough 126 is disposed closely beside the lower trough 125 such that the wires 121 and 122 are spaced closely together. When the pusher wires 121 and 122 are extended as shown in FIG. 9, a valley 123 is formed between the outermost points of the pusher wires 121 and 122. This valley 123 can be used to help position the valve cutter 100 when it is in use, as further discussed herein. Note that the valley 123 is generally aligned with the longitudinal center of the cutting blade 119. This means that when the valley 23 is contacting a portion of the cardiac valve, the center of the cutting blade 119 should be aligned with an opposite portion of the cardiac valve.

The cutter 100 further comprises a proximal pressure port 132 and a distal pressure port 133. The proximal pressure port 132 is located above the cutting blade 119 and the distal pressure port 133 is located below the cutting blade 119. The proximal pressure port 132 and distal pressure port 133 are of a type known in the art for measuring the pressure inside a patient's heart. For example, the pressure ports 132 and 133 may be channels with microcatheters that communicate with pressure transducers external to the cutter 100. Or, for example, the pressure ports may comprise pressure wires. In use of the cutter 100, the proximal pressure port 132 is typically used to measure the pressure proximal to the valve and the distal pressure port 133 is used to measure the pressure distal to the valve, as is discussed further herein.

Figure 10:
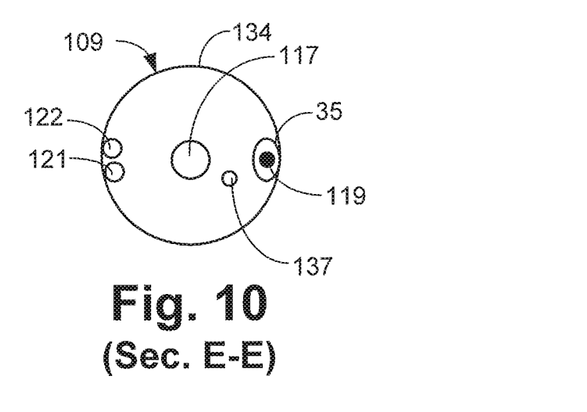
FIG. 10 is a cross sectional of e valve cutter of FIG. 9, taken along section lines E-E.

FIG. 10 is a cross-sectional representation of the upper portion 111 (FIG. 9) Of the cutter 100 of FIG. 9, taken along section lines E-E. An outer wall 134 extends generally circularly around the perimeter of the housing 109. The upper portion 111 has a diameter of 14 French in one embodiment, though other sizes may be used. The lumen 117 is centrally disposed within the housing 109 in the illustrated embodiment. The cutting blade 119 is disposed near the outer wall 134, within a sheath 135. The sheath 135 is generally oval or cylindrical in shape and extends down through the housing 109. In the illustrated embodiment, the sheath 135 surrounds the cutting blade 119 down the length of the housing 109, except where the cutting trough 120 (FIG. 9) is located.

The pusher wires 121 and 122 are located on an opposite side from (i.e., generally 180 degrees apart from) the cutting blade 119 in the illustrated embodiment. The pusher wires 121 and 122 are located close together and very close to the edge of the external wall 136 as shown. This arrangement enables the pusher wires 121 and 122, where they extend from the troughs 126 and 125 (FIG. 9), to push against the valve leaflets (not shown) to assist in stabilizing the cutter 100 and advancing the cutting blade 119 toward the tissue being cut, as further discussed herein.

In one embodiment, pressure wires 137 extend through the housing 109 to the proximal pressure port 132 and distal pressure port 133. In other embodiments, the pressure ports 132 and 133 comprise microcatheters that communicate with pressure transducers external to the cutter.

Figure 11:
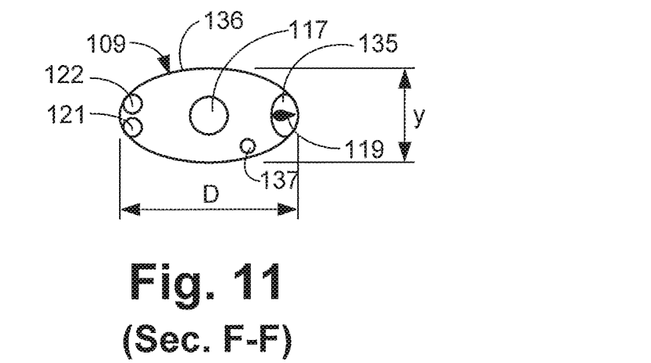
FIG. 11 is a cross sectional view of the valve cutter of FIG. 9, taken along section lines F-F.

FIG. 11 is a cross-sectional view of the elliptical middle portion 112 of the cutter 10 of FIG. 9, taken along section lines F-F. In the elliptical middle portion 112, an outer wall 136 is ovally shaped, with the cutting blade 119 and the pusher wires 121 and 122 disposed on opposite outermost sides of the oval as shown. The width "D" of the elliptical portion 112 of the cutter 100 is the same as the diameter of the upper portion 111 in the illustrated embodiment. The short side "y" of the elliptical portion 112 of the cutter 100 is substantially less than the width "D."

Figure 12:
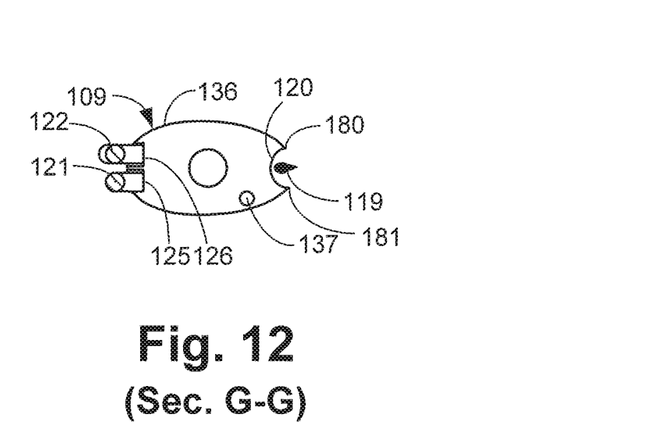
FIG. 12 is a cross sectional view of the valve cutter of FIG. 9, taken along section lines G-G.

FIG. 12 is a partial cross-sectional representation of the elliptical portion 112 of the cutter 100 of FIG. 9, taken along sections lines G-G. This figure shows the pusher wires 121 and 122 extended from the housing 109. In this extended position, the pusher wires 121 and 122 extend beyond the outer wall 136 as shown.

In this cross-sectional view, the cutting blade 119 appears as if it is extended from the cutting trough 120. However, the cutting blade 119 is generally vertically disposed within the housing 109. Because the outer wall 136 is cut away at the location of the cutting trough 120, the cutting blade 119 becomes the outermost surface at the location of the cutting trough 120, such that the cutting blade 119 may cut any tissue it contacts if the cutting blade 119 is rotating. In other words, the cutting wire extends further outwardly than opposed longitudinal edges 180 and 181 of the cutting trough 20.

The operation of the pusher wires 121 and 122 is substantially similar to that of the pusher wires 21 and 22 (FIG. 1), and the discussion of the pusher wires 21 and 22 in FIGS. 5 and 6 applies in this embodiment as well. Further, the operation of the cutter described with reference to FIG. 7 applies to this embodiment as well.

Figure 13:
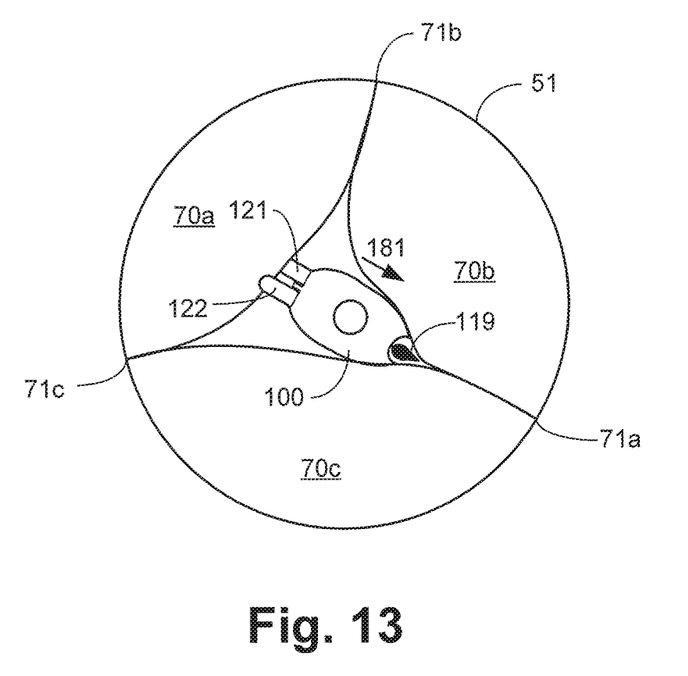
FIG. 13 is a cross sectional view of the valve cutter of FIG. 9 in operation.

FIG. 13 is a cross sectional view of the cutter 100 (similar to FIG. 8), with the cutter 100 in a patient's cardiac valve. In this view the cutter pusher wires 121 and 122 are pressing against a leaflet 70a of the cardiac valve 51. The pressing of the pusher wires 121 and 122 stabilizes the cutter within the cardiac valve and also causes the cutter 100 to move in the direction indicated by directional arrow 181, such that the cutting wire 119 advances to cut along a commissure 71a between the leaflets 70b and 70c of the aortic valve 51.

The pressure readings from the proximal pressure port 132 and distal pressure port 133 can be monitored during the cutting procedure. As the cuts are made to reduce the aortic stenosis, the systolic pressure reading from the distal pressure port 133 should begin to equalize with the reading from the proximal pressure port 132.

The invention claimed is:

1. A device for cutting cardiac valve, the device comprising:
    a housing comprising a single lumen adapted to receive a guide wire, the housing comprising an exterior wall;
    a high speed cutting blade disposed within the housing near the exterior wall of the housing;
    a motor configured to effectuate motion of the high speed cutting blade;
    an elongated cutout in the exterior wall adjacent to the cutting blade, the
    elongated cutout forming a cutting trough through which the cutting blade is accessible;

a first pusher wire and a second pusher wire disposed within the housing near the exterior wall of the housing, on an opposite side of the housing from the cutting trough, the first pusher wire and the second pusher wire each extendable through the exterior wall via a pusher wire trough associated with each of the first pusher wire and the second pusher wire, the pusher wire troughs comprising elongated cutouts in the exterior wall, the pusher wire troughs spaced apart from one another longitudinally such that when the first pusher wire and the second pusher wire are extended from the pusher wire troughs, a valley is formed between the first pusher wire and the second pusher wire.

2. The device of claim 1, wherein the cutting blade comprises a high speed reciprocating saw blade.

3. The device of claim 1, further comprising a proximal pressure port disposed upwardly from the cutting blade and a distal pressure port disposed downwardly from the cutting blade.

4. The device of claim 1, further comprising a proximal pressure wire disposed upwardly from the cutting blade and a distal pressure wire disposed downwardly from the cutting blade.

5. The device of claim 1, wherein the pusher wires are affixed at a bottom end of the pusher wire troughs and advancing the pusher wires from an upper end of the device causes the pusher wires to bow out from the pusher wire troughs.

6. The device of claim 1, wherein the housing comprises a tapered distal tip.

7. The device of claim 1, further comprising a substantially cylindrical upper portion and a substantially oval middle portion with a first transition portion transitioning the substantially cylindrical upper portion to the substantially oval middle portion, wherein the cutting trough and the pusher wire troughs each are disposed within the substantially oval middle portion.

8. The device of claim 7, further comprising a substantially cylindrical lower portion with a second transition portion transitioning the substantially oval middle portion to the substantially cylindrical lower portion.

9. The device of claim 7, wherein the cutting trough is disposed along a short side of the substantially oval middle portion and the pusher wire troughs are disposed along an opposite short side of the substantially oval middle portion.

10. The device of claim 7, wherein opposed longitudinal edges of the cutting trough are disposed inwardly from the cutting blade.

* * * * *